US006638498B2

(12) United States Patent
Green et al.

(10) Patent No.: US 6,638,498 B2
(45) Date of Patent: Oct. 28, 2003

(54) MOLECULARLY IMPRINTED POLYMERS FOR THE TREATMENT AND DIAGNOSIS OF MEDICAL CONDITIONS

(75) Inventors: Bernard S. Green, Kibbutz Yavne (IL); Morris Priwler, Modi'in (IL)

(73) Assignee: Semorex Inc., North Brunswick, NJ (US)

(*) Notice: Subject to any disclaimer, the term of this patent is extended or adjusted under 35 U.S.C. 154(b) by 26 days.

(21) Appl. No.: 09/893,643

(22) Filed: Jun. 29, 2001

(65) Prior Publication Data

US 2002/0015690 A1 Feb. 7, 2002

Related U.S. Application Data

(60) Provisional application No. 60/215,882, filed on Jun. 30, 2000.

(51) Int. Cl.[7] .......................... A61K 31/74; A61K 47/48
(52) U.S. Cl. .................... 424/78.17; 424/451; 424/464; 424/489; 424/436; 424/78.08; 424/164.1
(58) Field of Search .......................... 424/489, 464, 424/78.08, 78.17, 164.1, 436, 451

(56) References Cited

U.S. PATENT DOCUMENTS 5,858,296 A * 1/1999 Domb .................... 264/330

* cited by examiner

Primary Examiner—Thurman K. Page
Assistant Examiner—Liliana Di Nola-Baron
(74) Attorney, Agent, or Firm—G. E. Ehrlich (1995) Ltd.

(57) ABSTRACT

Improved molecularly imprinted polymers (MIPs) with both higher and more specific binding capacity for particular bile acids and/or salts, including the synthesis of such MIPs, the compounds themselves, and specific applications thereof. As an example of a particularly preferred specific application of these compounds, the present invention encompasses the use of the MIPs as sequestrants in the gastrointestinal tract, particularly in order to bind and therefore remove toxins from the gastrointestinal tract. In addition, the present invention is also useful for treatment of various diseases which are related to, and/or characterized by, an effect of bile acids and salts, such as atherosclerosis, liver disease and various diseases of the gastrointestinal tract. The MIP compounds of the present invention are also useful for combination therapy with other medications and for diagnosis and monitoring of diseases.

13 Claims, 2 Drawing Sheets

MOLECULARLY IMPRINTED POLYMERS FOR THE TREATMENT AND DIAGNOSIS OF MEDICAL CONDITIONS

This Application claims priority from US Provisional Application No. 60/215,882, filed on Jun. 30, 2000, which is currently pending.

FIELD OF THE INVENTION

The present invention is related to novel molecularly imprinted polymers, and in particular to improvements in the production of molecularly imprinted polymers (MIPs), as well as to these specific MIPs, and to the use of MIPs for specific applications. The MIPs of the present invention are particularly suitable for binding to, and thereby removing, toxins in the gastrointestinal tract. As an exemplary implementation, the present invention is described with regard to the removal of bile acids and bile salts from the gastrointestinal tract. In addition, the present invention is also useful for treatment of various diseases which are related to, and/or characterized by an effect of, bile acids and bile salts, such as atherosclerosis, cancer, liver disease and various diseases of the gastrointestinal tract. The MIP compounds of the present invention are also useful for combination therapy with other medications. These medications may involve mechanisms of action that lower or change the composition of bile acids and salts in the body or by a different mechanism. In addition the present invention also is useful for the diagnosis and monitoring of various diseases by selectively binding to an established marker which is then identified using known binding indicator techniques such as fluorescence. As an illustrative example for implementation, the present invention is described with regard to the diagnosis of medical conditions which are related to, and or characterized by an effect of, bile acids and/or bile salts, such as atherosclerosis, various diseases of the gastrointestinal tract, cancer and inflammatory conditions. This is achieved by determining the level of at least one specific bile acid or salt or the ratio of at least one specific bile acid or to at least a second specific bile acid or salt and determining whether these levels fall within an establish range which indicates the potential existence of the relevant disease. The analysis is performed on bile acids and or bile salts found in serum, bile, gastric contents, and feces.

BACKGROUND OF THE INVENTION

Figure 1A:
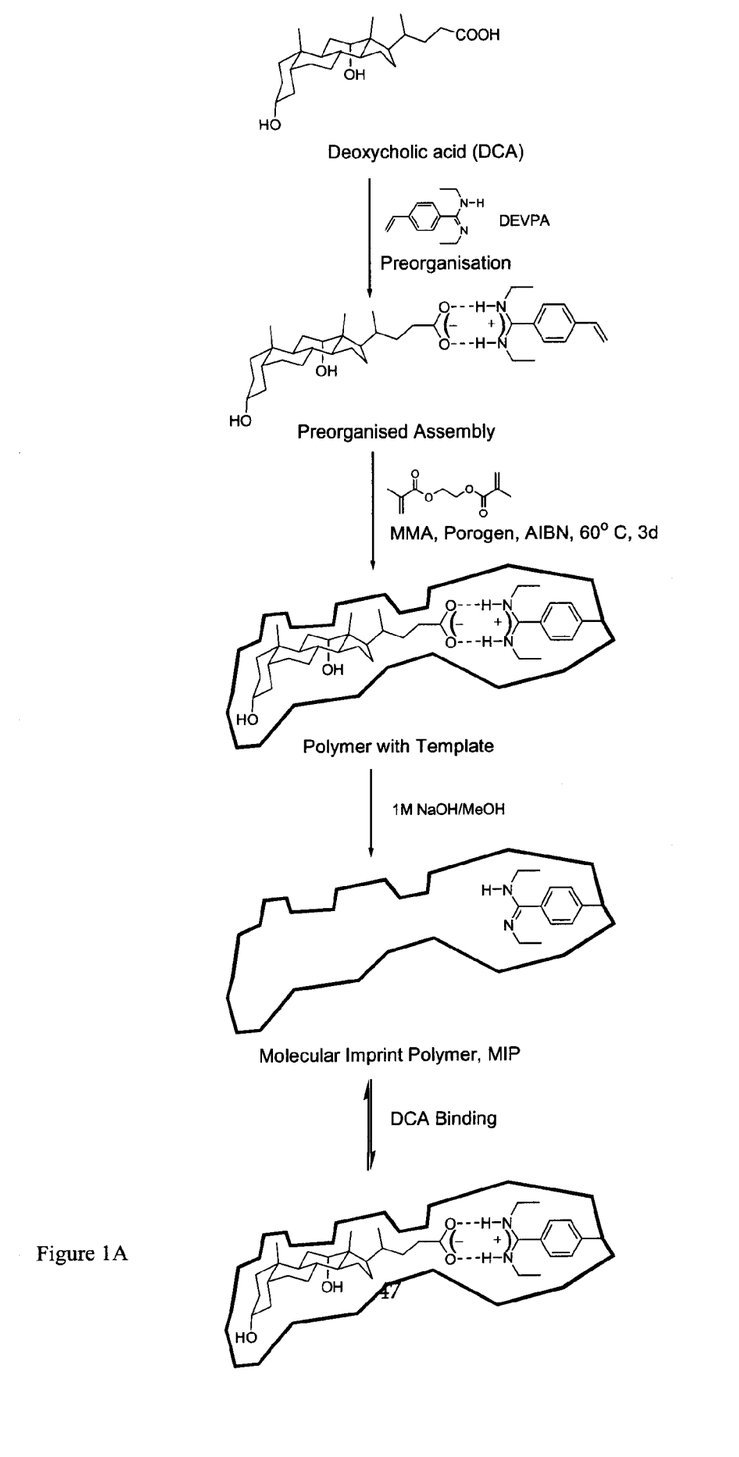
FIGS. 1A and 1B are schematic descriptions of methods for making and using the compounds of the present invention.
Figure 1B:
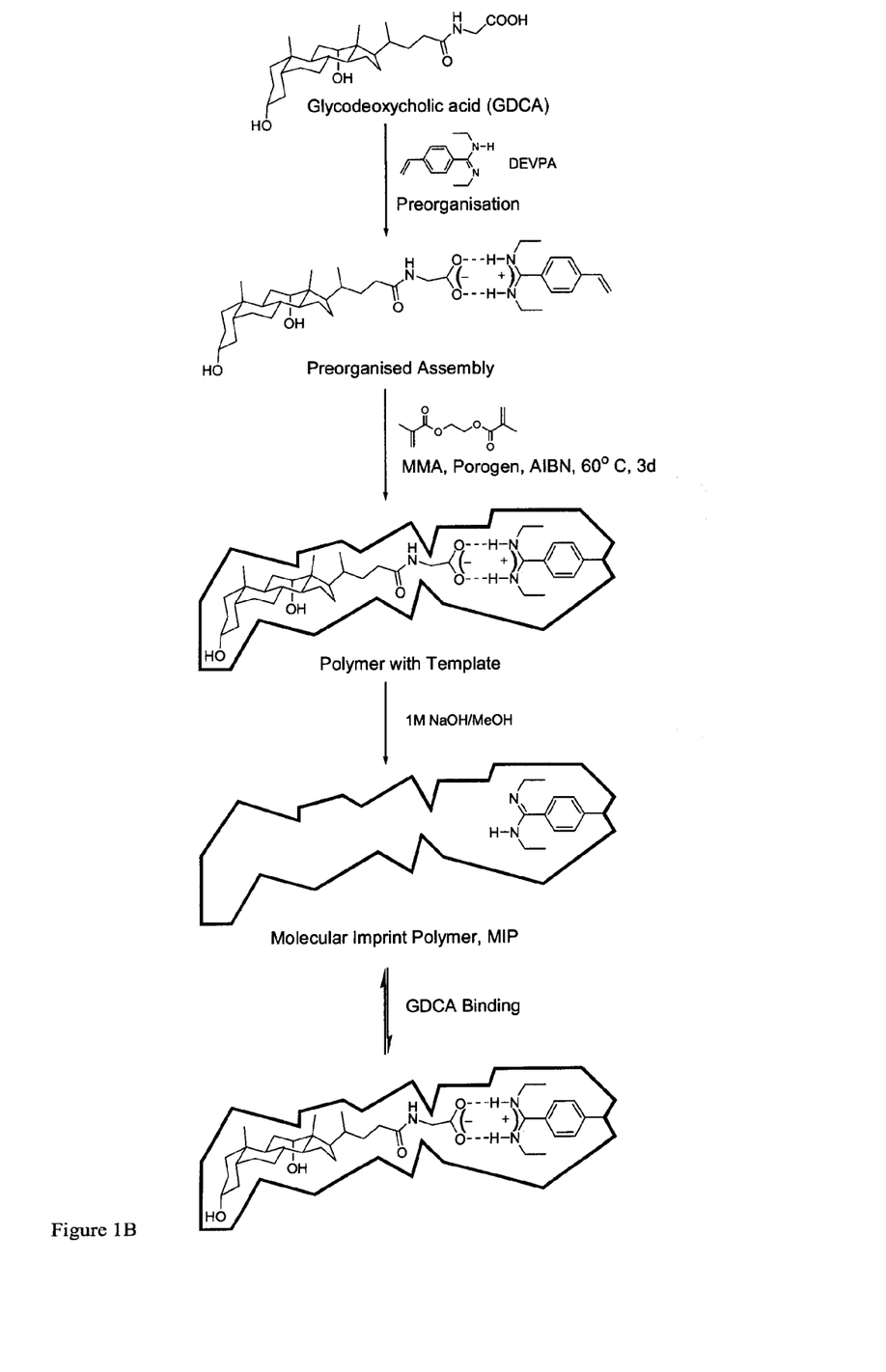

The subject of molecularly imprinted polymers has been extensively reviewed (e.g., G. Wulff, *Angew. Chem., Int. Ed. Engl.* 1995, 34, 1812–1832; A. G. Mayyes and K. Mosbach, *Trends Anal. Chem.* 1997, 16, 321–332; E. N. Vulfson, C. Alexander, and M. J. Whitcombe *Chem. Brit.* 1997, 33, 23–26; K. Haupt and K. Mosbach, *Trends Biotechnol.* 1998, 16, 468–475; *Molecular and Ionic Recognition with Imprinted Polymers*, ACS Symp. Ser. 703; R. A. Bartsch and M. Maeda, Eds.; American Chemical Society, Washington, D.C., 1998) and a number of patents on this topic have been issued [e.g., U.S. Pat. No. 4,127,730 (Wulff, G., Sarhan A.); U.S. Pat. No. 5,110,833 (Mosbach. K.); U.S. Pat. No. 5,630,978 (Domb, A.,); U.S. Pat. No. 5,587,273 (Yan, M. et al.); U.S. Pat. No. 5,872,198 (Mosbach, K. et al;)]. A schematic depiction of the formation of MIPs for deoxycholic acid (DCA) and glycodeoxycholic acid (GDCA) is shown in FIGS. 1A and 1B. Although the binding/recognition site is actually a family of non-homogeneous sites, the scheme illustrates how the cavities for two similar substances may differ.

The synthesis of MIPs, including those described with regard to the present invention in the "Description of the Preferred Embodiments" below, is performed with functional monomers. The monomers which were used for the present invention include all of the monomers listed in the following section. The synthesis of these monomers and related derivatives and analogs can be performed by organic chemists of ordinary skill in the art. It should be noted that although the present invention is described with regard to MIPs which bind bile acids and bile salts, this is for the purposes of description only and is not intended to be limiting in any way.

Bile Acid Sequestrants.

A number of polymers, such as cholestyramine, are used as bile acid sequestrants. Their action is based on the presence of strongly basic groups in the polymer (typically, ion exchange resin type of polymers) and they are used for cholesterol lowering and bile-related diseases. These materials are limited because they have limited potency and they also remove (bind) other required substances such as nutrients, drugs, etc. In addition, they often irritate the bowel and are not convenient or palatable to the patient. Accordingly there is a need for improved bile sequestrants. Selective MIPs which bind bile acids and salts do not remove needed nutrients, drugs or other substances and will be more potent; they will have low or no bowel irritation and have improved dosages. Importantly, the MIPs can be made so that they are selective to the more hydrophobic bile acids such as deoxycholic acid. Research shows that the more hydrophobic bile acids inhibit the removal of LDL from the blood stream and lead to a higher cholesterol blood serum level (Hueman, D. M. et al., *J Lipid Res.* 30: 1161, 1989).

While bile acids and salts serve important functions in the body, such as promoting digestion of fat, researchers have found that the more hydrophobic (water-resistant) bile acids, such as deoxycholic acid (DCA), chenodeoxycholic acid (CDCA) and lithocholic acid (LCA) facilitate higher absorption of lipids such as cholesterol and fats into the blood stream and are toxic, causing damage to cells and promoting cancer. Current research indicates that these more hydrophobic bile acids are highly significant disease-causing agents.

Additionally, research has implicated specific bile acids and bile salts as contributing to a number of diseases. For example, DCA has been implicated in the following:

Gallstones (Low-Beer, T. S., et al., *Lancet* (1978) 2:1063–65

Colorectal cancer (Ochsenkuhn, T. et al., *American Cancer Society* (1999) 1664–69; Hylemon P., *Journal of Lipid Research* (1997); Bernstein C. et al., *Cancer Research* (1999) 59, 2353–2357.)

Barrett's esophaghus and erosive esophagitis (Nehre D et al., *Gut,* (1999) 44(5) 598–602; Kauer et al., *Surgery,* (1997) 122(5) 874–81)

Arteriosclerosis caused by the presence of Oxidized LDL (Fuhrman B et al., *Free Radic Biol Med* 34-461997).

Inflammatory conditions promoted by the presence of COX-2 (Zhang et al., *J Biol Chem* (1998) 273(4):2424–8).

Clearly, improved compounds such as MIPS are required with both higher and more specific binding capacity to these particular bile acids and bile salts. Furthernore, such MIPs would be useful for the treatment and/or prevention of diseases which are at least partially caused by, or otherwise related to, these specific bile acids and/or salts. Unfortunately, such MIPs are not currently available.

illustrative example

SUMMARY OF THE INVENTION

The background art neither teaches nor suggests MIPs with both higher and more specific binding capacity for particular bile acids and/or salts, for the treatment and/or prevention of diseases which are at least partially caused by, or otherwise related to, specific bile acids and/or salts.

The present invention is of improved MIPs with both higher and more specific binding capacity, including the synthesis of such MILPs, the compounds themselves, and specific applications thereof. The MIP compounds of the present invention have the advantage of being adaptable for specific targeted therapeutic and diagnostic uses and/or functionality, thereby enabling treatment and diagnosis to be more effectively performed.

As an example of a particularly preferred specific application of these compounds, the present invention encompasses the use of MIPs as sequestrants in the gastrointestinal tract, particularly in order to bind and therefore remove toxins from the gastrointestinal tract.

As a particularly preferred example of such toxins, the compounds of the present invention are useful for the binding and removal of specific bile acids and/or salts. Examples of such bile acids and/or salts include, but are not limited to, a bile acid such as deoxycholic acid (DCA) or the tauro- or glyco-conjugates of DCA. The bile acid or bile conjugate is optionally chenodeoxycholic acid (CDCA) and the glyco or tauro conjugates thereof, or lithocholic acid (LCA) and the glyco or tauro conjugates thereof.

These bile acids and salts are targeted for removal because of their role in various disease states. For example, although bile acids and salts serve important functions in the body, such as promoting digestion of fat, more hydrophobic (water-resistant) bile acids, such as DCA, CDCA and LCA, facilitate higher absorption of lipids such as cholesterol and fats into the blood stream and are toxic, causing damage to cells and promoting cancer. Therefore, these more hydrophobic bile acids are highly significant disease-causing agents.

The novel molecularly imprinted polymers (MIPs) of the present invention are able to specifically target and remove significant proportions of these more hydrophobic bile acids. At present there is no drug that selectively targets the removal of hydrophobic bile acids from the body.

The present invention also encompasses the use of these MIP compounds for the treatment and/or prevention of diseases which are at least partially caused by, or otherwise related to, specific bile acids and/or salts. Examples of such diseases include, but are not limited to, heart disease, particularly by lowering cholesterol levels; treatment of heart and other oxidized LDL-initiated diseases such as cancer and inflammatory conditions by lowering oxidized LDL; cholesterol-related gallstones; colorectal cancer and its precursors; inflammatory disease initiated by the presence of Cox-2, gastro-esophageal reflux diseases (GERD) including Barrett's esophagus, corrosive esophagitis, and esophageal cancer. In addition, the present invention encompasses the use of such compounds to concurrently treat and/or prevent two or more of the above diseases.

The present invention also encompasses use of the MIP medication in combination with other medications where there is a need for more effective treatment which cannot be achieved by the MIP medication alone. These medications may involve mechanisms of action that lower or change the composition of bile acids and/or salts in the body or by a different mechanism.

The present invention also encompasses the use of the compounds of this invention for diagnosis and monitoring of compounds by binding to a marker and using known binding indicator techniques such as fluorescence. The analysis is performed on samples taken from the body. In a particularly preferred example, the compounds of the present invention are useful for the diagnosis and monitoring of specific bile acids and salts. Examples of such bile acids and salts include, but are not limited to, a bile acid such as deoxycholic acid (DCA) or the tauro- or glyco-conjugates of DCA. The bile acid or bile conjugate is optionally chenodeoxycholic acid (CDCA) and the glyco or tauro conjugates thereof, or lithocholic acid (LCA) and the glyco or tauro conjugates thereof.

These bile acids and salts may be targeted for diagnosis and monitoring because of their roles in various disease states. For example, although bile acids serve important functions in the body, such as promoting digestion of fat, more hydrophobic (water-resistant) bile acids, such as DCA, CDCA and LCA, are toxic, causing damage to cells and promoting cancer. Therefore, these more hydrophobic bile acids are highly significant disease-causing agents.

The novel molecularly imprinted polymers (MIPs) of the present invention are able to specifically bind these hydrophobic bile acids, and then to be detected by using known binding indicator techniques such as fluorescence, for thereby quantifying the levels of the more hydrophobic bile acids.

The present invention also encompasses the use of these MIP compounds for the monitoring and diagnosis of diseases which are at least partially caused by, or otherwise related to, specific bile acids and/or salts. Examples of such diseases include, but are not limited to, colorectal cancer and its precursors; and esophageal diseases including Barrett's esophagus, erosive esophagitis, and esophageal cancer by monitoring the levels of at least one bile acid or salts or the ratios of at least one bile acid or salts to other bile acids and/or salts.

The present invention solves a number of long-felt needs. There is a need for more effective medication, for example, with patients who do not respond to conventional treatment, and/or have severe conditions for which the currently available medication is insufficient for the required treatment. This may be achieved with the use of MIP therapy, alone or optionally in combination with other medication. The use of combination therapy is well established. These optional, additional medications may operate according to mechanisms of action that lower or change the composition of bile acids and/or salts in the body or by a different mechanism.

There is the need for simple screening techniques for diagnosis and monitoring, especially for asymptomatic conditions. An illustrative example is treatment of cancer where the earlier diagnosis of the cancer or pre-cancerous condition can significantly impact on the success of treatment and also contribute to preventing the condition. In some cases there is need for improving and simplifying existing methods; in others no existing method exists. MIPs have been used for the diagnosis and monitoring of various diseases by selectively binding to an established marker which is then identified using known binding indicator techniques such as fluorescence. In many cases there will be a need for the improved MIPs to achieve the required sensitivity.

As an example for implementation, the present invention is described with regard to the use of MIPs for diagnosis of medical conditions which are related to, and or characterized by, an effect of bile acids and/or bile salts, such as atherosclerosis, various diseases of the gastrointestinal tract, cancer and inflammatory conditions. This is achieved by determining the level of at least one specific bile acid or the ratio of at least one specific bile acid to at least a second specific bile acid and determining whether these levels fall within an establish range which indicates the potential existence of the relevant disease. The analysis is performed on bile acids and or bile salts found in serum, bile, gastric contents, and feces.

Hereinafter, the term "treatment" or "treat" for a disease state also includes the prevention of the occurrence of one or more symptoms and/or effects of the disease state itself. Hereinafter, the term "bile acid" includes both conjugated and unconjugated bile acids unless otherwise indicated.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of improved MIPs with both higher and more specific binding capacity, including the synthesis of such MIPs, the compounds themselves, and specific applications thereof. In addition, the present invention is also useful for treatment of various diseases which are related to, and/or characterized by an effect of, bile acids, such as atherosclerosis, liver disease and various diseases of the gastrointestinal tract. The MIP compounds of the present invention are also useful for combination therapy with other medications.

The compounds of the present invention are improved MIPs. According to a preferred embodiment of the present invention, the compound comprises a molecularly imprinted polymer featuring at least one functional monomer selected from the group consisting of: 2-, 3- and 4-vinyl-2-hydroxypyridine; the family of functional monomers 4-vinylbenzamide and N-methyl (and other N-alkyl) derivatives, i.e., N-alkyl-(4-vinylbenzamide) derivatives, and N,N-dimethyl-, N-methyl, N-alkyl-, and N,N-dialkyl-(4-vinylbenzamide) derivatives. Preferably, the functional monomers are cross-linked with at least one crosslinking agent which is an N,N'-(4-vinylbenzoyl)-1,ω-diaminoalkane. According to other preferred embodiments of the present invention, the molecularly imprinted polymer features at least one functional monomer of DEVPA (N,N'-diethyl(4-vinylphenyl)amidine). More preferably, the molecularly imprinted polymer features at least one additional functional monomer, including acrylamide, methacrylamide, N-methylacrylamide, N-methylmethacrylamide, and related derivatives or analogs of these, substances. Most preferably, the crosslinking agent for linking the functional monomers is ethyleneglycol dimethacrylate, N,N'-diacryloyl- or N,N'-dimethacryloyl ethylenediamine or mixtures of these and related derivatives or analogs of these substances.

Alternatively, the crosslinking agent is selected from the group consisting of N,N'-diacryloyl- or N,N'-dimethacryloyl 1,3-diaminobenzene, N,N'-diacryloyl- or N,N'-dimethacryloyl 1,4-diaminobenzene, the diacrylates or dimethacrylates of 1,2-, 1,3-, or 1,4-dihydroxybenzene as well as N,N'-(4-vinylbenzoyl)-1,ω-diaminoalkane.

Also alternatively, the crosslinking agent is selected from the group consisting of an N,N'-diacryloyl- or N,N'-dimethacryloyl 1,ω-diaminoalkane.

As an example of a particularly preferred specific application of these compounds, the present invention encompasses the use of the MIPs as sequestrants in the gastrointestinal tract, particularly in order to bind and therefore remove toxins from the gastrointestinal tract.

As a particularly preferred example of such toxins, the compounds of the present invention are useful for the binding and removal of specific bile acids and/or salts. Examples of such bile acids and/or salts include, but are not limited to, a bile acid such as deoxycholic acid (DCA) or the tauro- or glyco-conjugates of DCA, but may optionally be chenodeoxycholic acid and the glyco or tauro conjugates thereof, or lithocholic acid and the glyco or tauro conjugates thereof.

The present invention encompasses the use of these compounds for the treatment and/or prevention of diseases which are at least partially caused by, or otherwise related to, specific bile acids and/or salts. Examples of such diseases include, but are not limited to, heart disease, particularly by lowering cholesterol levels; treatment of heart and other oxidized LDL-initiated diseases such as cancer and inflammatory conditions by lowering oxidized LDL; cholesterol-related gallstones; colorectal cancer and its precursors; and esophageal diseases including Barrett's esophagus, erosive esophagitis, and esophageal cancer and its precursors. In addition, the present invention encompasses the use of such compounds to concurrently treat and/or prevent two or more of the above diseases.

EXAMPLE 1

Method for Synthesis of the Compounds of the Present Invention

The following description is intended as a non-limiting example of methods for synthesizing the compounds of the present invention, by forming the molecularly imprinted polymers from the selected functional monomer groups.

Monomer Synthesis and Characterization.

A large variety of functional monomers were synthesized in order to be able to choose a mix of substances that would afford optimal performance in bile acid and bile salt binding. These included DEVPA (N,N'-diethyl(4-vinylphenyl)amidine) [G. Wulff, T. Gross, R. Schoenfeld *Angew. Chem., Int. Ed. Engl.* 1997, 36, 1962;. G. Wulff, R. Schoenfeldt, M. Gruen, R. Baumstark, G. Wildburg, L. Haussling, German Patent, BASF Aktiengesellschaft, 9610, O.Z. 0050/46933, 1994], and the commonly used functional monomers including methyl methacrylate, acrylamide, methacrylamide, N-methylacrylamide, N-methyl-methacrylamide, and related derivatives or analogs of these substances as described in the above-mentioned reviews on molecularly imprinted polymers.

The functional monomers 2-, 3- and 4-vinyl-2-hydroxypyridine were also used. The family of functional monomers 4-vinylbenzamide and N-methyl (and other N-alkyl) derivatives, i.e., N-alkyl-(4-vinylbenzamide) derivatives, and N,N-dimethyl-, N-methyl, N-alkyl-, and N,N-dialkyl-(4-vinylbenzamide) derivatives were also used. The binding constants of various functional monomers with bile acids and bile salts were determined using published methods. Thus, the binding constant for complexation of DEVPA and glycodeoxycholic acid was established as $Ka=1.4\times10^3$ $M^{-1}$, in DMSO-$d_6$ at 16° C., using the single point NMR method [D. A. Stauffer, R. E. Barrans, Jr., and D. A. Dougherty, *J. Org. Chem.*, 55, 2762–2767 (1990)].

Polymer Synthesis.

The MIPs were prepared using methods in the literature as referenced above and modifications of these methods. The methods included bulk polymerization and suspension polymerization with heating and with irradiation initiation using AIBN and related initiators of polymerization. For both bulk polymerization and suspension polymerization at least two functional monomers were used in addition to at least one crosslinker. Bulk polymerization proceeded using DMF, ethanol, ethanol-acetonitrile, acetonitrile, DMSO, and mixes of these solvents as the porogen. The polymerization solutions or mixtures were degassed using three freeze-evacuate-thaw cycles and flame-sealed in glass tubes. The suspension polymerization followed methods used as previously published (Svec, et. al., *Angew. Macromol. Chem.*, 7, 135 (1975). Typically, a dispersion phase of 0.1 to 1-wt. % polyvinyl pyrolidone, 0.2 to 2-wt % polyvinyl alcohol in water, and an organic phase consisting of the bile acid or salt, monomers and crosslinker(s) in octanol/cyclohexanol mixtures.

Table 1 presents illustrative examples of MIPs prepared using bile acids and bile salts as the template/imprint molecules.

A more specific, non-limiting example is described with regard to CDCA. CDCA-binding polymer MS39 (capacity= 187 micromol/g=1.47 mg of CDCA/20 mg of MS39) was allowed to stand in aqueous ethanolic solutions of CDCA for 20 hrs, containing various levels of CDCA; it was previously shown that this time was sufficient for attaining equilibrium binding. The analyses of CDCA were achieved using the above-mentioned spectroscopic method (A. Fini and P. Zuman, 1993). In this way, the binding capacity and calibration curves and specificity of the CDCA-binding polymer MS39 were determined. Thus, in one of the above experiments, MS39 absorbed 1.15+/−0.04 mg of CDCA while a control polymer absorbed 0.17+/−0.05 mg of CDCA under identical conditions.

For diagnostic assays, CDCA-binding polymer was charged with tritium-labelled CDCA. The release of radiolabeled CDCA was monitored under specified conditions and also in the presence of varying levels of "cold" CDCA. In this way, it was possible to accurately estimate CDCA in unknown samples. In a modification of this method, the MIP was prepared as a thin layer in the wells of microtiter plates; the plates were incubated with tritium-labelled CDCA, washed, and then used to prepare calibration curves and for the assay of CDCA.

In a different modification of the above, a fluorescent derivative of cholic acid, in which the 12-alpha position was

TABLE 1

Composition and characterization of MIPS[a]

| MIP | Template | Porogen | Template removal | Surface area ($m^2/g$) | Pore volume (ml/g) | Porosity | Mean pore radius (nm) |
|---|---|---|---|---|---|---|---|
| P1 | GDCA | MeCN + EtOH (1:1 v/v) | 94% | 116 | 1.243 | 61.8% | 21.4 |
| P2 | CDCA | EtOH | 90% | 129 | 1.437 | 65.1% | 22.3 |
| P3 | LCA | THF | 77+% | 145 | 1.094 | 58.7% | 15.1 |

[a]The steroid template, DEVPA, methl methacrylate, and ethylene glycol dimethacrylate were dissolved in porogen (solvent) in the molare ratio of 1:1:5:25, respectively; AIBN was added to the clear solution. The solution was degassed using three freeze-evacuate-thaw cycles and flame-sealed in a glass tube, which was then placed in an oven at 60° C. for 3 days. The resulting polymer was ground and sieved to 45—125 μm; the template was removed by treating with 1M NaOH to obtain the corresponding MIPs.

Binding Studies.

The binding experiments were performed using literature procedures for related substances [M. J. Whitcombe, M. E. Rodrigues, P. Villan, E. N. Vulfson, *J. Am. Chem. Soc.*, 117, 7105–7111 (1995)]. The dried polymers (1–40 mg) were weighed into 2-mil screw-cap vials and 1 ml of a 50% aqueous ethanolic ligand solution (50 iM) were added to the vials which were then placed in a sample shaker overnight.

For analysis of bile acids, the polymer suspensions were very cautiously filtered directly into fresh screw-cap vials containing 3-ml of conc. sulfuric acid, cooled in ice. The solutions were maintained at 80° C. for one hour and then cooled to room temperature. They were then analyzed by UV-VIS spectroscopy using a UVIKON-930 instrument according to a reported method [A. Fini and P. Zuman, *Collect. Czech. Chem. Commun.* 58, 53 (1993)]. For each bile acid and bile salt a selected wavelength was used and the ligand concentration was determined by reference to a calibration curve which was prepared using five samples of known concentration. All determinations were performed in duplicate. The wavelengths used for each analyte was as follows: deoxycholic acid, 385 nm; glycodeoxycholic acid and tauro deoxycholic acid, 309 nm; chenodeoxycholic acid, 382 nm; lithocholic acid, 308 nm.

substituted with a fluorophore such as coumarin, was used as the assay substance. CDCA-binding MIPs were charged with this fluorescent-labelled CDCA-analog and used to develop both a microplate and a free MIP particle assay for CDCA.

EXAMPLE 2

Methods and Compositions for Administration

The compounds of the present invention can be administered to a subject by various ways, which are well known in the art. Hereinafter, the term "subject" refers to the human or lower animal to whom the therapeutic agent is administered. For example, administration may be done topically (including ophthalmically, vaginally, rectally, intranasally and by inhalation), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to the compound of the present invention. Persons of ordinary skill in the art can easily determine optimum dosages, dosing methodologies and repetition rates.

EXAMPLE 3

Method of Treatment of Bile Salt or Acid-related Conditions

As noted above, the compounds of the present invention are believed to be useful for the treatment of disease states which are related to bile acids, by binding to and thereby removing the bile acid from the gastrointestinal tract of the subject. The following example is an illustration only of a method of treating such a condition with the compound of the present invention, and is not intended to be limiting.

The method includes the step of administering a compound, in a pharmaceutically acceptable carrier as described in Example 2 above, to a subject to be treated. The compound is administered according to an effective dosing methodology, preferably until a predefined endpoint is reached, such as the absence of a symptom of the disease condition in the subject, or the prevention of the appearance of such a symptom in the subject.

Examples of such diseases, disease conditions or disease states include, but are not limited to, heart disease, treatment of heart and other oxidized LDL-initiated diseases such as cancer and inflammatory conditions, cholesterol gallstone, colorectal cancer and its precursors, esophagus diseases including Barrett's esophagus, erosive esophagitis esophageal cancer and its precursors and COX-2 mediated inflammatory conditions. These disease conditions are described in more detail in the subsections below.

Reduction of Cholesterol Levels

There is a well-established relationship between cholesterol lowering and reduction in atherosclerosis and heart disease. Over 6 million patients in the US use cholesterol-lowering drugs and it is estimated that 25 million people in the US should be taking cholesterol-lowering drugs. Statins (i.e., inhibitors of HMG CoA reductase, the enzyme required for the body's production of cholesterol) are the main class of drug used.

Bile sequestrants have been used for many years as the first level drug treatment for cholesterol reduction. Its use has been limited, and is even decreasing, because it is inconvenient to use, requiring high dosages and not palatable. Geltex Pharmaceuticals Inc. (F.D.A. N.D.A 21-141, N.D.A. 21-176) has sought to overcome these disadvantages and obtained FDA approval for new polymeric bile sequestrants. However, these still require significant dosages and other desirable nutrients may be removed.

The MIPs provide a convenient and selective bile-sequestrant which, unlike existing polymeric agents, do not remove desirable substances (e.g., vitamins and medications). Another advantage is that removing the more hydrophobic bile acids will have a greater impact on reducing cholesterol than the removal of other bile acids because the hydrophobic bile acids promote the presence of cholesterol in the blood (Reno Z. et al. in *Gastroenterology Clinics of North America,* ed. Cooper A. D., W. B. Saunders Company (1999) p.1; Cooper A. D., in *Gastroenterology Clinics of North America,* ed. Cooper A. D. W.B.Saunders Company (1999) p. 211).

Particular cholesterol lowering applications where the specific bile sequestrant MIPs will be preferred include, but are not limited to, the following examples. First, for patients with high risk of cholesterol and the other medical indications where the removal of the more hydrophobic bile acids is warranted, the MIP compounds of the present invention are preferred. Examples include high-risk colon cancer patients, patients with Barrett's esophagus and at a high risk of gallstones due to dieting. Other suitable candidates include young patients who need to take cholesterol lowering drugs long-term to avoid potential damage to the liver; and patients requiring combination therapy with statins, for example, patients with very high cholesterol levels.

Reduction of Oxidized LDL

In the past decade it has been recognized that oxidized LDL and not LDL is the real culprit in heart disease. It damages the lining of blood vessels, causes growth of cells that form the wall of the blood vessel and causes thickening and narrowing of the blood vessel—all of which are recognized to contribute to heart attacks and strokes. Thus, there is a need to reduce the oxidation of LDL.

In vitro research has demonstrated that DCA can induce the conversion of LDL to oxidized LDL. Bile acids are exposed to LDL when they circulate in the blood. (Ljubuncic P. et al., Gut (1996); 39: 475–8).

From the intestine, bile acids enter into the portal vascular system where they are associated with plasma and lipoproteins. Biophysical properties of primary or secondary bile acids dictate whether they associate with lipoproteins or albumin as is most often the case or if they are freely soluble in plasma. Approx. 10%–30% of bile acids in the portal system escape subsequent extraction by the liver and spill over into the systemic circulation. As a result the blood vessels of the heart are exposed to DCA in the bile acids. The reduction of DCA then is used to reduce the level of oxidized LDL.

The MIP compounds of the present invention may be preferred as a combined cholesterol and oxidized LDL lowering medication or in combination with statins as the mechanism of action is different.

Treatment of GERD & Esophagus Cancer

Gastro-esophageal Reflux Disease (GERD) refers to a range of symptoms that result from the exposure of the esophagus to gastric acid. Heartburn and regurgitation are the most common symptoms. Approximately 10% of the American population experience heartburn daily. Although GERD is a manageable disease it can evolve into erosive esophagitis where there is inflammation and tissue damage to the esophagus. If left untreated, complications may occur including hemorrhage and Barrett's esophagus. An estimated and rapidly increasing 1–2 million American patients (average age 55–65) progress to Barrett's esophagus (i.e., changes in the appearance of the lining of the esophagus). Over the course of time, 5–10% of these patients will develop esophagus cancer which has a very poor survival rate (i.e., 5% in 5 years). Barrett's esophagus leads to a 30–40 fold increase in the risk of esophagus cancer, the fastest growing cancer in Western countries.

Currently, the main medication for severe GERD (esophagitis and Barrett's Esophagus) are drugs that block production of acid and relieve irritated tissue. The most effective drugs are proton pump inhibitors with weaker histamine H2 receptor antagonists also sometimes prescribed. The combination of gastric juice and bile acids in esophagus patients is considered decisive in the development of many cases of Barrett's esophagus. Additionally, recent studies have shown that many patients with erosive esophagus and Barrett's esophagus have significantly higher concentrations of the more toxic hydrophobic bile acids and overall bile acid concentrations in the esophagus. In healthy patients this normally is not the case (Nebra D., et al., Gut, (1999); 44:598;Kauer W. K. H. et al., Surgery (1997); 122:874–81). Research also indicates that exposure to bile acids and in particular DCA and CDCA are decisive factors contributing to the development cancer (Zhang et al., J Biol Chem (1998); 273:2424–8; Shirvani et al. Gastroenterology 2000; 118: 487–496).

The medication that suppresses gastric juice does not halt the reflux itself. Even if medication renders a GERD patient asymptomatic, this does not always indicate complete control of the reflux and asymptomatic reflux will lead to progression of Barrett's esophagus. Furthermore, the pharmacologically altered gastric contents, particularly bile acids, may contribute to the progression of Barrett's esophagus. Significantly, the bile appears to be decisive for the development of adenocarcinoma (Demeester T. R., "Without Bile—No Adenocarcinoma with Barrett's Esophagus", Presented at International Workshop "From Reflux to Barrett's Carcinoma," Mar. 23–25, 1998, European Surgical Institute). Recent research suggests that a reason for this effect may be that gastric acid suppression treatment leads to bacterial overgrowth including species that deconjugate bile. This leads to a significant increase in the concentration of unconjugated bile acids (Shido K et al., Gut 1998 42(2): 266–71; Thieson J. et al., J Gastointest Surg 2000 4(1): 50–4).

As a result of the limitations of existing medical treatment with acid suppressants, anti-reflux surgery is being considered. It also has not proven effective in many cases to lead to the regression of Barrett's esophagus and the risk of cancer remains. It is considered controversial whether surgery should be performed on all individuals with Barrett's esophagus especially those whose symptoms are well controlled with medication. Photodynamic therapy also is being used in clinical trials in an effort to remove the lesions and anti-cancerous medication are being examined for treating the Barrett's esophagus lesions. However they do not treat the cause and there are concerns that these approaches may only partially prevent the progression to cancer.

Accordingly, there is a need for alternative treatments. The specific bile acid binding MIPs offer an alternative medical approach for treatment of severe GERD and Barrett's esophagus. Removal of the most toxic bile acids in the gastrointestinal tract before they enter the esophagus should limit the development of severe GERD and Barrett's esophagus and assist in the healing process. Combination therapy with the gastric juice suppressants may be particularly effective in preventing Barrett's esophagus with asymptomatic patients who may still suffer from reflux and in overcoming the potential for the proton pump inhibitors contributing to the progression of Barrett's esophagus.

Furthermore, bile acids have been found at higher pH levels with unconjugated bile acids (e.g., DCA) being most gastrotoxic under these conditions. There are significant numbers of non-responders to the gastric acid inhibitor medication and the MIPs may be used to treat non-responders where the reason is the presence of bile acids at the higher pH levels.

Since these bile acids are decisive in the development of adenocarcinoma, the specific bile acid binding MIPs may prove effective in promoting the regression of esophagus lesions. They may prove very effective in combination with the photodynamic therapy-based cancerous and pre-cancerous killing agents being developed for use to treat Barrett's esophagus.

Treatment of Colon Cancer

Colorectal cancer is one of the most lethal cancers. In the USA it is the number two killer cancer with nearly 55,000 deaths and 140,000 new cases annually. High risk groups include those with a family history of polyps, over the age of 50, patients who have had colon polyps removed and who have had colon cancer (over 1.2 million people in the US).

Colorectal cancer provides unique opportunities for primary intervention among human malignancies because it progresses through clinically recognizable stages from normal mucosa through enlarging and increasingly dysplastic polyps which eventuate in carcinoma.

The precursor relationship of colorectal adenoma to carcinoma and the high prevalence of adenomas make them an attractive target in chemoprevention. The prevalence of polyps increases with age in moderate and high-risk populations, reaching 20–40% at the age of 50–60 years, and 50% or more for individuals older than 70 years. The steepest increase in adenoma prevalence occurs between the ages of 50–59. However, removal of polyps does not change the pathogenetic milieu responsible for their growth and development. The recurrence rate for colorectal adenomas has been variably reported, but most studies document an adenoma recurrence rate of 20–60% after two years. For patients who had newly diagnosed adenomas removed during colonoscopy, 28% had additional polyps detected at a one-year follow-up examination, and of those patients, 22% had new adenomatous polyps again detected on examination two years later. Patients who have undergone surgical resection of a primary colorectal cancer have also been shown to be at high risk of developing metachronous adenomas. Thus, there is a need for additional treatment to prevent the recurrence of the polyps.

The cyclooxygenase-2 (COX-2) inhibitor, Celebrex, has been approved for adjuvant treatment of colon polyps. However, the highest reported reduction rate has been 28% (FDA approved labeling). Thus, there remains the need for improved treatment. Other approaches are revealed in Larson et al. (U.S. Pat. No. 5,945,411) where ursodeoxycholic acid is used in combination with sulindac and phenolic NSAID to prevent the recurrence of colorectal adenomas following removal. However the ursodeoxycholic acid is not selective and the amount of the more toxic bile it removes is limited.

Recent research with more precise sampling supports a connection between DCA and colorectal cancer (Bayerdorffer E. et al., Gut (1995); 36: 268–273; Ochsen-kuhn T. et al., Cancer (1999), 85: 1664–1669). Although only a small fraction of bile acids in the enterohepatic circulation enter the colon; perturbations of the cycling rate of bile acids by diet (e.g., fat), mucosal dysfunction such as Crohn's disease or surgery (e.g., cholecystectomy) may increase the fecal bile acid load or reduce bile acid uptake and cause spillage into the colon. Thus, the reduction of DCA and its removal from the colon can be used as an alternative preventive of the pre-cancerous polyps. The MIPs also can be used in combination with other treatments such as Celebrex medication.

Research also suggests that DCA may increase the proliferation rate of colon cancer cells. Thus, DCA removal may also be a useful supplemental treatment for treating colon cancer (Peiffer L P. et al., Dig Dis Sci, (1997) 42(11):2234–40), This can be alone or in combination with other colon cancer medications such as Celebrex or specific cancer or pre-cancerous killing agents such as the compounds being developed by Cell Pathways Inc.

Treatment of Liver Disease

Cholestatic diseases are a group of diseases characterized by the progressive retention of bile acids in the liver, resulting in liver injury, cirrhosis and ultimately death. In the USA, primary biliary cirrhosis (PBC) occurs in about 10,000–40,000 patients and primary sclerosing cholangitis (PSC) in about 2,500–16,000 patients. Other cholestatic conditions include: complications of liver or bone marrow transplantations, complications of cystic fibrosis, neonatal cholestatic syndromes, cholestasis of pregnancy, autoimmune cholangiopathy, as well as a variety of drug reactions.

Ursodeoxycholic acid (UDCA) slows the rate of disease progression, lessens the morbidity and mortality risk and improves quality of life. In PBC, UDCA can postpone the need for liver transplantation. The probable mechanism of action of UDCA in PBC may reflect the observation that UDCA changes the amount of toxic hydrophobic and non-toxic hydrophilic bile acids in the bile salt pool in favor of nontoxic bile. When the bile cannuliculae are damaged by an autoimmune or other disease process inherent to any of the cholestatic diseases, bile salts leak into the hepatic parenchyma. The resulting inflammation and the extent of bile salt induced injury is a direct result of the concentration of toxic hydrophobic bile salts present in the extravasated bile (Oude Elferink R. P. J. and Groen, A. K. in *Gastroenterology Clinics of North America*, Vol 28, ed. Cooper A. D., W.B.Saunders Company (1999) pp.59–74; Salen G. and Batta, A. K. *Gastroenterology Clinics of North America*, Vol 28, ed. Cooper A. D., W.B.Saunders Company (1999) pp.173–193; Stiehl A., Benz, C. and Sauer, P. *Gastroenterology Clinics of North America*, Vol 28, ed. Cooper A. D., W.B.Saunders Company (1999) pp.195–209).

Many patients with cholestatic liver diseases do not respond to UCDA therapy. This includes patients with advanced disease and some familial intrahepatic cholestasis patients. Lack of response may reflect an upper limit of how much UDCA can be absorbed so that approximately half of the UDCA administered is absorbed under the best of circumstances.

Generalized pruritus (itchiness) is a very troublesome symptom in chronic cholestasis. Many patients with pruritus have become suicidal from their discomfort. Although incompletely understood, the pathogenesis is believed to be related to the accumulation of toxic bile acids in the skin. Combined UDCA treatment with bile acid sequestrants active in the intestine is a partially successful treatment. By themselves, bile acid sequestrants are not very effective, probably for a number of reasons.

For example, bile acid sequestrants do not differentiate between the toxic hydrophobic and nontoxic hydrophilic bile acids such as UCDA. As they are non-specific, when given with UDCA, they absorb the UDCA reducing the effectiveness of this non-toxic bile salt treatment.

They do not decrease the overall level of bile acids because additional bile acids (toxic and nontoxic) will be produced. The liver regulates the amount of bile salts in the body. As the concentration of one relative to the other changes, the overall amount of bile salts remains the same. Thus, a treatment that indiscriminately sequesters bile salts only serves to stimulate more production of both toxic and non-toxic bile salt species.

These bile acid sequestrants also bind fat-soluble vitamins such as vitamin D, K, and E and hydrophobic medications. The long-term use of these sequestrants can lead to vitamin deficiencies such as bone disease and clotting abnormalities. They also may cause variable delivery of medication with the potential for under dosing.

Thus there is a need for alternative treatment. The MIP compounds of the present invention offer alternative improved treatment used alone to remove the more toxic bile acids and/or salts or as combination therapy with UDCA for improved treatment of pruritus, when the UDCA alone is not effective, and to improve overall prognosis in conditions that warrant UDCA therapy. The MIPs are selective for the toxic bile acids and overcome these problems for a number of reasons.

First, the MIP compounds of the present invention do not bind UDCA in significant levels. Theoretically, orally administered UCDA absorption will not be affected by our MIPs and the proportion of total bile salts that are UCDA will increase in bile, making extrabiliary bile both less hydrophobic and less toxic.

In addition, it is possible to target the most hydrophobic and toxic bile acids, thereby changing the balance between toxic and nontoxic bile acids and thus reducing the overall toxic levels. As the MIPs remove the toxic bile salts, the proportion of total bile that is UCDA will increase. Since the liver attempts to keep the pool of bile salts constant and orally administered UCDA is replacing the removed toxic bile salts, the liver will not be stimulated to replenish the bile salt pool with toxic bile salts.

In addition, because the compounds of the present invention do not bind other fat-soluble substances such as vitamin D, E, and K or other hydrophobic medications, the potential for hypovitaminosis or undermedication as a consequence of their use is low.

Treatment of Cholesterol Gallstones

Approximately 10–15% of the adult population have gallstones. In the USA more than 20 million have gallstones with about one-third developing symptoms. The prevalence is higher in women, obesity (rapid weight loss) as well as in older patients and certain ethnic groups. Gallstones are the most common and costly disease in the USA with an estimated overall cost of more than $5 billion with over 500,000–600,000 people undergoing surgery to remove the gallbladder. Most gallstones are composed principally of cholesterol.

Typical treatment for patients with symptoms requiring treatment is surgical removal of the gallbladder unless they are unable to tolerate general anesthesia or have a condition that precludes surgery. Drawbacks of the surgery include recurring pain and possible contribution to gallbladder and colon cancer.

Oral dissolution therapy with UDCA is most effective in 15% of symptomatic patients (small non-calcified floating cholesterol stones of less than 5 mms have 90% chance of dissolution and stones less than 10 mms have 60% chance of dissolution). Six to twelve months of therapy are required in many patients and monitoring is necessary until dissolution is achieved.

This treatment is used when operation is not possible and for patients who choose to avoid operation or for prophylactic treatment for special groups, e.g., diabetic patients, sickle cell patients, children pre-transplantation and/or immuno-suppressed patients and for patients undergoing rapid weight loss. The main drawback is the recurrence of gallstones (in about half of those treated stones return within 5 years).

Deoxycholic acid is implicated in gallstone disease. Cholesterol hypersecretion triggers events that lead to loss of gallbladder reservoir function leading to increased degradation of primary bile salts to secondary bile salts (such as DCA) by the bacteria in the intestine. This leads to an increased proportion of DCA which enhances cholesterol hypersecretion into bile and also accelerates cholesterol crystallization (Beer F. et al, J Clin Invest (1992); 90:859–868; Shoda J. et al., Hepatology (1995); 21:1291–1302).

It has been found that after gallstone patients were treated with antibiotics that kill the bacteria converting cholic acid to DCA, their DCA levels and cholesterol supersaturated bile dropped below the threshold required to develop gallstones. However, broad-scale antibiotics are not practical as a treatment because they tend to wipe out both "good" and "bad" bacteria in the intestine.

The reduction of DCA by the MIP compounds of the present invention, in combination with the administration of UDCA, are effective as an alternative oral treatment to reduce cholesterol supersaturated bile, to shorten the time required for dissolution, to be more effective for larger stones and reduce the risk of recurrence.

Anti-inflammatory Effects

The cyclooxygenase -2 (COX-2) inhibitors have been shown to exhibit anti-inflammatory effects. Research shows that DCA and CDCA promote the expression of COX-2 (Zhang et al., J Biol Chem (1998); 273:2424–8; Shirvani et al. Gastroenterology 2000; 118: 487–496).

From the intestine, bile acids enter into the portal vascular system where they are associated with plasma and lipoproteins. Biophysical properties of primary or secondary bile acids dictate whether they associate with lipoproteins or albumin as is most often the case or if they are freely soluble in plasma. Approx. 10%–30% of bile acids in the portal system escape subsequent extraction by the liver and spill over into the systemic circulation. The bile that circulates in the blood can enhance the expression of COX-2 production so that its reduction will have an anti-inflammatory effect, for example, in treating rheumatoid arthritis.

The MIP compounds of the present invention could be used alone or in combination with other anti-inflammatory drugs such as Celebrex.

In addition to using MIPs to sequester and remove bile acids, the use of MIPs is described, in combination with other non-specific medications which can reduce the level of the more toxic bile acids, such as non-MIP polymer bile sequestrants (e.g., colesevelam hydrochloride developed by Geltex Pharmaceuticals Inc.), UDCA or its derivatives which replace the more toxic bile acids. Additionally, the MIPs may be used with antibiotic or other agents to prevent the conversion of the relatively harmless cholic acid to the toxic deoxycholic acid by 7-alpha-dehydroxylating bacteria (Berr F. et al. Gastroenterology (1996) 111:1611–1620).

Alternatively, these agents that can reduce the levels of the more toxic bile may be used to treat new medical indications including advanced GERD (esophagitis, Barret's esophagus), esophagus cancer, oxidized LDL for atherosclerosis and anti-inflammatory treatment.

EXAMPLE 4

Method of Treatment of Bile Salt or Acid-related Conditions using MIPs in Combination with Other Medication As noted above, the compounds of the present invention may not be sufficiently effective for the treatment of disease states which are related to bile acids, by binding to and thereby removing the bile acid from the gastrointestinal tract of the subject. In order to achieve the desired treatment, the compounds of the present invention may be used in combination with other medications. The medications may involve mechanisms of action that lower or change the composition of bile acids and/or salts in the body or act by a different mechanism. It is important to note that since the MIPs are selective, there is only a very limited possibility that the MIPs will bind with the combination therapy medication, as has occurred for example when non-specific bile sequestrants are used in combination therapy causing in some cases variable delivery of medication with the potential for under-dosing.

The following example is an illustration only of a method of treating such a condition with the compound of the present invention, and is not intended to be limiting.

The method includes the step of administering a MIP compound, in a pharmaceutically acceptable carrier as described in Example 2 above, together with another medication to a subject to be treated. The compounds are administered according to an effective dosing methodology, for example together or separately, and preferably until a predefined endpoint is reached, such as the absence of a symptom of the disease condition in the subject, or the prevention of the appearance of such a symptom in the subject.

Illustrative but not limiting examples of medication for altering the level or composition of bile acids in the body include the following.

Bile sequestrants have been used for many years as the first level drug treatment for cholesterol reduction. Its use has been limited and is even reducing because it is very inconvenient to use, requiring very high dosages and is not palatable. Geltex Pharmaceuticals Inc. (F.D.A. N.D.A 21-141, N.D.A. 21-176) has sought to overcome these disadvantages and obtained FDA approval for new polymeric bile sequestrants. However, these still require significant dosages and other desirable nutrients may be removed.

These bile sequestrants have been used before in combination therapy with ursodeoxycholic acid (UDCA) for treatment of liver cholestatic diseases but the limitations particularly there ability to bind the UDCA has limited their effectiveness (Oude Elferink R. P. J. and Groen, A. K. in *Gastroenterology Clinics of North America*, Vol 28, ed. Cooper A. D., W.B.Saunders Company (1999) pp.59–74. Salen G. and Batta, A. K. *Gastroenterology Clinics of North America*, Vol 28, ed. Cooper A. D., W.B.Saunders Company (1999) pp.173–193. Stiehl A., Benz, C. and Sauer, P. *Gastroenterology Clinics of North America*, Vol 28, ed. Cooper A. D., W.B.Saunders Company (1999) pp.195–209. Cooper A. D., in *Gastroenterology Clinics of North America* ed. Cooper A. D. W.B.Saunders Company (1999) p. 211).

Ursodeoxycholic acid (UDCA) is a non-toxic bile acid which is also used for the treatment of gallstones and primary biliary cirrhosis. It has been used with limited success in combination therapy with non-specific bile sequestrants for primary biliary cirrhosis, especially for the treatment of pruritis. (Oude Elferink R. P. J. and Groen, A. K. in *Gastroenterology Clinics of North America*, Vol 28, ed. Cooper A. D., W.B.Saunders Company (1999) pp.59–74. Salen G. and Batta, A. K. *Gastroenterology Clinics of North America*, Vol 28, ed. Cooper A. D., W.B.Saunders Company (1999) pp.173–193. Stiehl A., Benz, C. and Sauer, P. *Gastroenterology Clinics of North America*, Vol 28, ed. Cooper A. D., W.B.Saunders Company (1999) pp.195–209. Cooper A. D., in *Gastroenterology Clinics of North America* ed. Cooper A. D. W.B.Saunders Company (1999) p. 211).

Bile acids are absorbed from the small intestine by a passive and an active mechanism. Bile acid transport inhibitors are being developed for treating bile related disease (Glaxo Welcome 264w94 in Phase II clinical trials and U.S. Pat. No. 5,589,358; Cooper A. D., in *Gastroenterology Clinics of North America* ed. Cooper A. D. W. B. Saunders Company (1999) p. 211). These will have the effect of reducing bile circulated in the body. Antibiotics have been used to kill the 7 alpha-dehydroxylating bacteria that enhance deoxycholic acid input by converting cholic acid to DCA (Beer F. et al *Gastroenterology* 1996 Dec; 111(6): 1611–2), P. Hylemon of Virginia Commonwealth University, in cooperation with and Hoechst Marion Roussel, is developing specific inhibitors of the bacteria in the colon that convert cholic acid to DCA. Other approaches to inhibit these bacteria may also be considered. These approaches also may be used for the bacteria found to convert conjugated bile to unconjugated bile found for example when acid inhibitor medication is taken for GERD treatment (Thieson J. et al., J Gastointest Surg 2000 4(1): 50–4).

Antibodies may bind bile acids so that their activity is neutralized. Non-limiting examples of antibodies raised against bile acids include those outlined in U.S. Pat. Nos. 5,631,138 and 5,976,811.

Illustrative but not limiting examples of combination therapy of MIP with medication for altering the level or composition of bile acids in the body include the following.

Treatment of Liver Disease

As outlined in Example 3 above UDCA is used in treating PBC. The probable mechanism of action of UDCA in PBC may reflect the observation that UDCA changes the amount of toxic hydrophobic and non-toxic hydrophilic bile acids in the bile salt pool in favor of nontoxic bile (Oude Elferink R. P. J. and Groen, A. K. in *Gastroenterology Clinics of North America*, Vol 28, ed. Cooper A. D., W.B.Saunders Company (1999) pp.59–74. Salen G. and Batta, A. K. *Gastroenterology Clinics of North America*, Vol 28, ed. Cooper A. D., W.B.Saunders Company (1999) pp.173–193. Stiehl A., Benz, C. and Sauer, P. *Gastroenterology Clinics of North America*, Vol 28, ed. Cooper A. D., W.B.Saunders Company (1999) pp.195–209).

Also as outlined in example 3, there is a need for alternative treatment to UDCA. The MIP compounds of the present invention offer alternative improved treatment. However in other cases, use of the MIPs may be insufficient to remove the required levels of the more toxic bile acids and/or salts to effect the desired treatment. Combination therapy of the MIPs with UDCA may be effective for the improved treatment of cholestatic disease and pruritus, when the MIP alone is not effective, and to improve overall prognosis in conditions that warrant MIP therapy.

The MIP compounds of the present invention are ideal for combination therapy as they do not bind UDCA in significant levels. Orally administered UDCA absorption should not be affected by the MIP compounds and the proportion of UDCA total bile salts will increase in bile, making the bile both less hydrophobic and less toxic.

Treatment of Cholesterol Gallstones

As outlined in Example 3, specific MIPs that bind bile acids, particularly DCA. In severe or other cases, such MIPs may not be sufficient to achieve effective treatment especially of larger gallstones. The reduction of DCA by the MIP compounds of the present invention, in combination with the administration of UDCA, are effective as an alternative oral treatment to reduce cholesterol supersaturated bile, to shorten the time required for dissolution, to be more effective for larger stones and to reduce the risk of recurrence.

Illustrative but not limiting examples of combination therapy medication of MIPs with other medication that acts by a mechanism that does not alter the levels or composition of bile acids include:

Reduction of Cholesterol Levels

As outlined in example 3, bile-binding MIPs may be used to lower cholesterol. Where cholesterol levels are high, the MIP therapy alone or other cholesterol lowering therapy such as statin medications may not be sufficient. This approach has been applied with nonspecific bile sequestrants with some success (Geltex Pharmaceuticals Inc. F.D.A. N.D.A 21–141, N.D.A. 21–176). However, because they are non-specific, these sequestrants may interact with the statins leading to underdosing and reduced effect of the statins. As the MIPs and statins also have different mechanisms, they can be used together in combination therapy. The specific MIPs are unlikely to interact with the statins which could lead to underdosing or to reduced effect of the statins.

Treatment of GERD & Esophagus Cancer

As outlined in Example 3, the gastric acid inhibitors may not prevent bile acids from refluxing and causing GERD (esophagitis and Barrett's Esophagus) and contributing to the development of cancer. In fact, these medications may potentiate the damaging effects of bile acids by increasing the levels of bile or changing the bile composition form conjugated to the potentially more toxic unconjugated bile.

Combination therapy with the gastric juice suppressants may be particularly effective in preventing Barrett's esophagus with asymptomatic patients who still suffer from reflux, in overcoming the potential contribution of proton pump inhibitors to the progression of Barrett's esophagus and for non-responders.

Since these bile acids are decisive in the development of adenocarcinoma, the specific bile acid binding MIPs may prove effective in promoting the regression of esophagus lesions. They may prove very effective in combination with the photodynamic therapy-based cancerous and pre-cancerous killing agents such as those being developed by Cell Pathways Inc. for treating Barrett's esophagus.

Treatment of Colon Cancer

As outlined in Example 3 MIPs targeting specific toxic biles are used to treat colon polyps. The use of MIPs alone in severe or other cases may not be sufficient. In such cases, combination therapy of MIPs with other medication for such treatment may be used. Examples include the cyclooxygenase-2 (COX-2) inhibitor Celebrex , the pre-cancerous cell killing agents such as being developed by Cell Pathways Inc. and sulindac and phenolic NSAID.

Similarly the MIPs may be used to remove the DCA and other bile acids that may increase the proliferation rate of colon cancer cells, as well as supplemental colon cancer treatment in combination with other colon cancer medications, such as Celebrex, or with specific cancer or pre-cancerous killing agents, such as the compounds being developed by Cell Pathways Inc.

EXAMPLE 5

Diagnosis/Screening of Bile Acids

The MIP compounds of the present invention have been used for sensitive assays.

They have the advantage over other biological assays of enhanced stability, simple handling and long-life storage. They can be coated on the plates used for diagnosis, thus reducing handling during diagnosis. The MIPs binding the bile acids have the potential to provide novel and simple-to-handle diagnostic systems for the rapid and sensitive quantification of bile acids in serum, bile, gastric contents and feces.

The MIP compounds of the present invention could prove especially effective in screening for diseases where bile acids contribute to the development and progression of disease and for the monitoring of treatment.

Imprinted polymers have already been used successfully as substitutes for antibodies in immunoassays (Vlatkis G., et al., Nature 1993; 361:645–647). The specific bile acid-binding MIP compounds of the present invention can also be used in a variety of formats for sensitive assays for, respectively, DCA, CDCA, and other bile acids and their salts.

A more specific non-limiting example is described regarding use of a CDCA-binding MIP for a diagnostic assay. The CDCA-binding polymer was charged with tritium-labelled CDCA. The release of radiolabeled CDCA was monitored under specified conditions and also in the presence of varying levels of "cold" CDCA. In this way, it was possible to accurately estimate CDCA in unknown samples. In a modification of this method, the MIP was prepared as a thin layer in the wells of microtiter plates; the plates were incubated with tritium-labelled CDCA, washed, and then used to prepare calibration curves for the assay of CDCA.

In a different modification of the above, a fluorescent derivative of cholic acid, in which the 12-alpha position was substituted with a fluorophore such as coumarin, was used as the assay substance. CDCA-binding MIPs were charged with this fluorescent labelled CDCA-analog and used to develop both a microplate and a free MIP particle assay for CDCA.

One illustrative, non-limiting example of a method for diagnosis of a bile-related disease in a subject with the MIP compounds is as follows. First, a sample of serum is obtained from the subject. Next, the sample is contacted with an MIP compound to determine at least a relative amount of at least one bile acid in the tissue sample. This relative amount could be a specific level of at least one bile acid. Alternatively, it could be a ratio of at least a first bile acid to at least a second bile acid.

Non-limiting examples of suitable diseases are described in greater detail below.

Colon Cancer

Coloscopic procedures are the accepted method for diagnosing Colon cancer. Since this procedure is invasive and relatively costly, there is a need for diagnostic screening of colon cancer.

Research has shown a correlation in patients and controls between the levels of unconjugated DCA in the serum and high colonic proliferation rates of colorectal mucosa—considered the first stages of cancer (Ochsenkuhn T. et al., Cancer (1999), 85: 1664–1669). Additional research has suggested that colon cancer risk can be identified by monitoring bile acids and the changes in the ratio of DCA to cholic acid (Kamano T. et al. Dis Colon Rectum, (1999), 42(5):668–72).

GERD and Esophagus Cancer

One clinical approach being evaluated for patients with severe GERD and Barrett's esophagus is endoscopic surveillance to allow for the diagnosis of cancer at an early, treatable stage. For patients without dysplasia, endoscopic surveillance is recommended every 2–3 years and for patients with dysplasia every 6 months. However, endoscopy has been found to miss cancer in a high proportion of cases. Currently, the only method for detecting this condition is endoscopic surveillance.

Perhaps even more importantly, it is estimated that as many as half of the patients with Barrett's esophagus are asymptomatic. These patients may either progress to cancer without treatment or are treated at a late stage of cancer development. An alternative, more convenient, less intrusive and costly screening test is needed.

Monitoring the levels of secondary bile may prove effective as a first level screening of patients with Barrett's esophagus to identify high risk cancer patients or patients with GERD including asymptomatic patients that otherwise may not be detected until cancer has developed. Possible methods for the monitoring of bile levels include but are not limited to: screening secondary bile acid levels (Nehra D., et al., Gut, (1999); 44:598;Kauer W. K. H. et al., Surgery (1997); 122:874–81—where concentrations were found to be significantly higher than controls); detecting DCA and CDCA levels (Zhang et al., J Biol Chem (1998); 273:2424–8; Shirvani et al. Gastroenterology 2000; 118: 487–496—where DCA and CDCA were found to promote cancer development); the difference in ratios of conjugated to unconjugated bile acids (Shido K et al., Gut 1998 42(2): 266–71; Thieson J. et al., J Gastoinest Surg 2000 4(1): 50–4—research showing proton pump inhibitor treatment leads to a significant change in the ratio of conjugated to unconjugated bile).

It will be appreciated that the above descriptions are intended only to serve as examples, and that many other embodiments are possible within the spirit and the scope of the present invention, as defined in the claims which follow.

What is claimed is:

1. A method for treating a subject suffering from a presence of a toxin in the gastrointestinal tract, the method comprising administering a molecularly imprinted polymer to the gastrointestinal tract of the subject, wherein said molecularly imprinted polymer is capable of binding to the toxin and sequestering the toxin, and wherein said molecularly imprinted polymer comprises at least one functional monomer selected from the group consisting of: 2-, 3- and 4-vinyl-2-hydroxypyridine and N,N'-diethyl(4-vinylphenyl)amidine, and wherein said molecularly imprinted polymer further comprises a cross-linking agent for cross-linking said at least one functional monomer, wherein said crosslinking agent is selected from the group consisting of ethyleneglycol dimethacrylate, N,N'-diacryloyl- or N,N'-dimethacryloyl ethylenediamine, N,N'-diacryloyl- or N,N'-dimethacryloyl 1,3-diaminobenzene, N,N'-diacryloyl- or N,N'-dimethacryloyl 1,4-diaminobenzene, a diacrylate or dimethacrylate of 1,2-, 1,3-, or 1,4-dihydroxybenzene, N,N'-(4-vinylbenzoyl)-1,ω-diaminoalkane, and an N,N'-diacryloyl- or N,N'-dimethacryloyl 1,ω-diaminoalkane.

2. The method of claim 1, wherein the specific toxin is a bile acid or bile salt selected from the group consisting of deoxycholic acid (DCA), the tauro- or glyco-conjugates of DCA, cholic acid and tauro- or glyco-conjugates of cholic acid.

3. The method of claim 1, wherein the bile acid or bile salt is chenodeoxycholic acid and the glyco or tauro conjugates thereof, or lithocholic acid and the glyco or tauro conjugates thereof.

4. The method of claim 1, wherein the molecularly imprinted polymer features at least one functional monomer, DEVPA (N,N'-diethyl(4-vinylphenyl)amidine).

5. The method of claim 1, wherein the molecularly imprinted polymer features at least one functional monomer selected from the group consisting of analog or derivative of an amidine.

6. The method of claim 1, wherein the molecularly imprinted polymer features at least one functional monomer selected from the group consisting of acrylamide, methacrylamide, N-methylacrylamide, N-methylmethacrylamide, and derivatives or analogs thereof.

7. The method of claim 1, wherein said molecularly imprinted polymer specifically targets a bile acid and/or salt for removal from the gastrointestinal tract, such that the toxin comprises said bile acid and/or salt.

8. The method of claim 1, wherein the toxin comprises a bile acid and/or salt, the method further comprising treating a disease at least related to said bile acid and/or salt by administering an additional medication for treating the disease, wherein said molecularly imprinted polymer binds to said bile acid and/or salt for sequestration.

9. The method of claim 1, wherein said molecularly imprinted polymer is administered orally.

10. The method of claim 1, wherein said molecularly imprinted polymer is administered with a suppository.

11. The method of claim 1, wherein a template for said molecularly imprinted polymer comprises the toxin.

12. A method for treating a subject suffering from a presence of a toxin in the gastrointestinal tract, the method comprising administering a molecularly imprinted polymer to the gastrointestinal tract of the subject, wherein said molecularly imprinted polymer is capable of binding to the toxin and sequestering the toxin, and wherein said molecularly imprinted polymer is synthesized in the presence of the toxin as a template, and wherein said molecularly imprinted polymer comprises at least one functional monomer selected from the group consisting of: 2-, 3- and 4-vinyl-2-hydroxypyridine and N,N'-diethyl(4-vinylphenyl)amidine, and wherein said molecularly imprinted polymer further comprises a cross-linking agent for cross-linking said at least one functional monomer, wherein said crosslinking agent is selected from the group consisting of ethyleneglycol dimethacrylate, N,N'-diacryloyl- or N,N'-dimethacryloyl ethylenediamine, N,N'-diacryloyl- or N,N'-dimethacryloyl 1,3-diaminobenzene, N,N'-diacryloyl- or N,N'-dimethacryloyl 1,4-diaminobenzene, a diacrylate or dimethacrylate of 1,2-, 1,3-, or 1,4-dihydroxybenzene, N,N'-(4-vinylbenzoyl)-1,ω-diaminoalkane, and an N,N'-diacryloyl- or N,N'-dimethacryloyl 1,ω-diaminoalkane.

13. The method of claim 12, wherein said toxin comprises a bile acid and/or salt, such that said template comprises said bile acid and/or salt.

* * * * *